Figure 1:
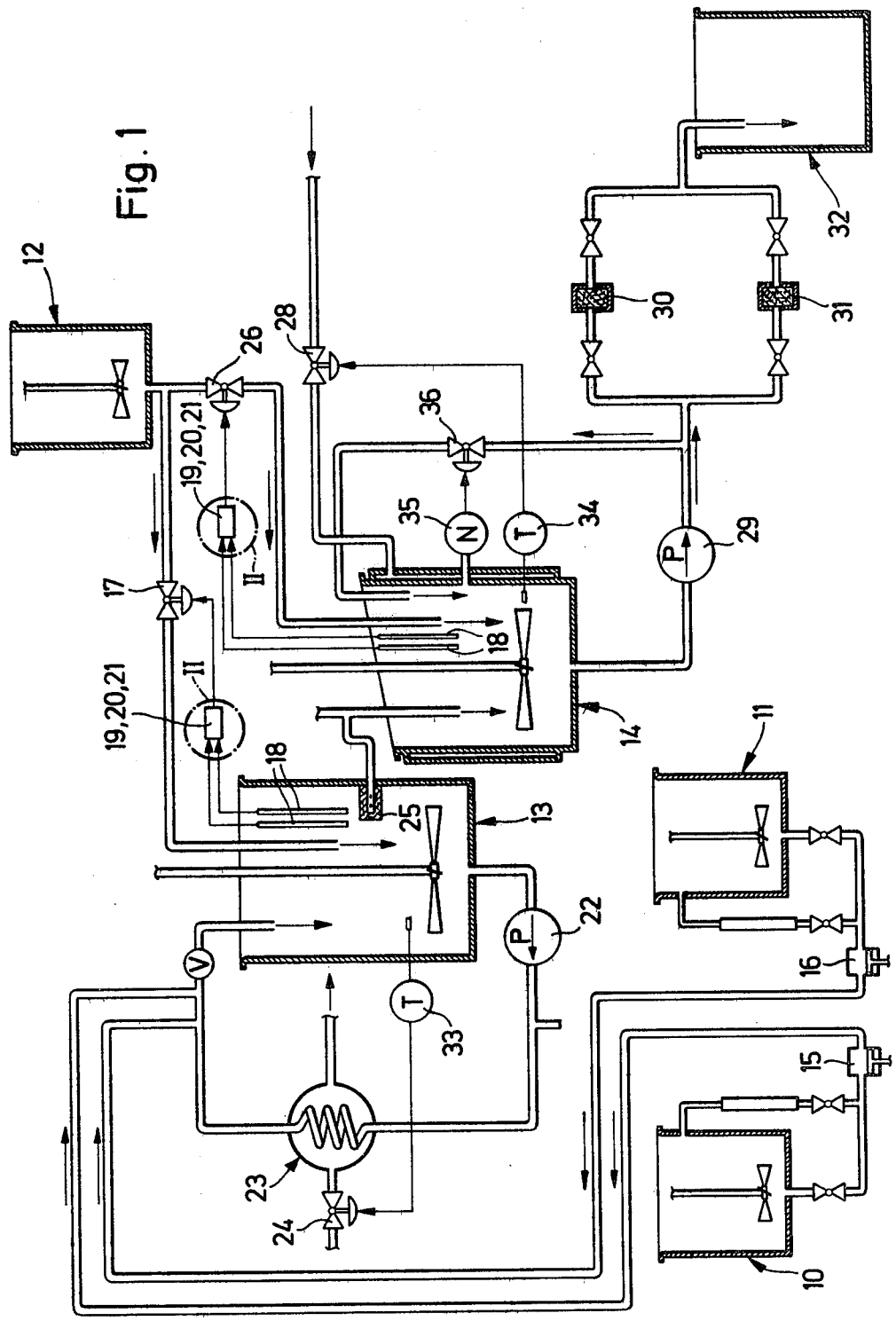

United States Patent [19]

Hamilton et al.

[11] 4,246,171

[45] Jan. 20, 1981

[54] CONTINUOUS DIAZOTIZATION PROCESS, WHEREIN THE RATE OF ADDITION OF INORGANIC NITRITE IS AUTOMATICALLY CONTROLLED BY POLAROVOLTRIC MEANS

[75] Inventors: Alexander Hamilton, Giffnock; Colin Nelson, Barrhead, both of Scotland

[73] Assignee: Ciba-Geigy Corporation, Ardsley, N.Y.

[21] Appl. No.: 940,414

[22] Filed: Sep. 7, 1978

Related U.S. Application Data

[63] Continuation-in-part of Ser. No. 875,364, Feb. 6, 1978, abandoned, which is a continuation of Ser. No. 711,891, Aug. 5, 1976, abandoned.

[51] Int. Cl.$^3$ ........................................... C07C 113/04
[52] U.S. Cl. .................................... 260/141; 260/142; 422/108; 422/110; 422/119; 422/187; 422/197
[58] Field of Search ................................ 260/141, 142

[56] References Cited

U.S. PATENT DOCUMENTS 3,117,954   1/1964   Hupfer ................................. 260/141

FOREIGN PATENT DOCUMENTS 540844   9/1955   Belgium ................................. 260/141

OTHER PUBLICATIONS

Buchler et al., Zeit. Anal. Chem., vol. 186, pp. 154–164 (1961).
Farbwerke (II), Chemical Abstracts, vol. 53, Item #21814a (1959).

Primary Examiner—Floyd D. Higel
Attorney, Agent, or Firm—Joseph F. DiPrima; Luther A. R. Hall

[57] ABSTRACT

Automatically controlled continuous process for the diazotization or tetrazotization of aromatic amines in which the rate of addition of the inorganic nitrite is controlled by a polarovoltric method. The process comprises adding regularly and continuously to a reactor an aqueous slurry or solution of the amine containing sufficient acid for the diazotization process and simultaneously adding to the reactor a solution of an inorganic nitrite at a rate which is automatically regulated by a polarovoltric controller to ensure that a preselected concentration of unreacted nitrous acid is maintained in the reactor throughout the whole period of the reaction.

10 Claims, 2 Drawing Figures

CONTINUOUS DIAZOTIZATION PROCESS, WHEREIN THE RATE OF ADDITION OF INORGANIC NITRITE IS AUTOMATICALLY CONTROLLED BY POLAROVOLTRIC MEANS

This is a continuation-in-part of application, Ser. No. 875,364, filed on Feb. 6, 1978, now abandoned, which is a continuation of application Ser. No. 711,891, filed on Aug. 5, 1976, now abandoned.

The present invention relates to the preparation of diazo compounds and more particularly to a method of automatic control of the diazotisation of aromatic amines on a continuous basis.

The diazotisation of aromatic amines is a fundamental step in the production of azo pigments. In the most common diazotisation process an aromatic primary amine is reacted with an inorganic nitrite usually sodium nitrite under aqueous acid conditions to give a diazonium compound which is usually obtained in solution form. The reaction may be represented by the following equation

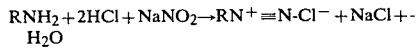

$$RNH_2 + 2HCl + NaNO_2 \rightarrow RN^+ \equiv N\text{-}Cl^- + NaCl + H_2O$$

in which R is an aromatic nucleus which may be substituted by groups such as alkyl, halogen, alkoxy, nitro, acylamino, carboxy, cyano, sulphonic acid or sulphonamido.

Diazotisation in aqueous acidic media may be carried out batch-wise or continuously. In a batch-wise process the amine is mixed to a smooth paste with water and hydrochloric acid in a mechanically stirred vessel and an aqueous solution of sodium nitrite is added. The reaction is practically quantitative.

There are two main parameters which vary using manual control on a batch-wise process. These are:

1. Temperature

With amines which give a fast reaction e.g. 3,3'-dichlorobenzidine, a very large amount of heat is released very quickly and since diazonium compounds are sensitive to heat, the heat evolved must be absorbed and this is usually done by having flake or crushed ice present in the reaction mixture to keep the temperature around 0° C. Although this method is very effective it entails the making and handling of large quantities of ice. In addition the process operator has to judge the amount of ice which should be added and if too little is added the temperature rises too high causing the quality of the diazo solution to suffer due to formation of unwanted by-products.

2. Rate of Addition of Sodium Nitrite

The sodium nitrite solution is added to the mixture of amine and acid at such a rate that a fairly heavy excess of sodium nitrite is maintained. This is controlled by a spot test method using filter-paper impregnated with a mixture of starch and potassium iodide. When excess of sodium nitrite is present in the reaction the test paper gives a blue spot and the rate of addition of sodium nitrite solution is controlled so that the reaction mixture gives a very dark blue spot on the test paper. Close control of the reaction manually requires a great degree of skill in order to reproduce conditions correctly in every batch because (a) if the sodium nitrite is not added fast enough an excess of nitrite is not maintained and a secondary reaction can take place with certain amines in which diazotised amine reacts with undiazotised amine to form a diazoamino compound and (b) if the sodium nitrite is added too fast so that a gross excess of nitrite is present other secondary reactions involving oxidation rather than diazotisation may take place.

These secondary reaction products cause difficulties when the diazo solution is being clarified and they also result in variations in the quality of the azo pigment produced from the diazo solution.

Continuous diazotisation processes have been developed in which the temperature and rate of addition of sodium nitrite are controlled automatically rather than manually and such processes are described in British Patent Specifications Nos. 812,368 and 844,062. These processes use a potentiometric technique using oxidation-reduction electrodes such as a platinum-calomel electrode system and a gold-calomel electrode system respectively to control the rate of addition of sodium nitrite.

The use of a polarovoltric control method in purely analytical titration systems for the determination of aromatic amines has been described by W. Büchler in Zeitschrift fur analytische Chemie Vol. 186 (1961) pp. 154–164 which teaches a greater end-point sensitivity of the polarovoltric method over the redox method at a specific sodium nitrite concentration. These titrations were carried out on a batch-wise basis.

We have found now that the polarovoltric method can also be used for the control of continuous diazotisation processes on a commercial production scale where it shows advantages over the redox methods previously described. It shows the improved end-point sensitivity described by Büchler and in addition we have found that the concentration of excess nitrite present in the reaction mixture can be controlled to any desired value within certain limits by variation of the polarising current. Such control has not been previously described. It is not possible using the previous redox methods nor is it a feature of the analytical method of the Büchler paper. It is especially valuable in commercial diazotisation processes which are normally carried out in a series of two or more reaction vessels since it allows the possibility of maintaining a relatively high excess of nitrite in reaction vessels towards the start of the process where the reaction is still incomplete and a very slight excess in the last reaction vessel where the reaction should be complete. The polarovoltric method thus shows increased sensitivity at higher concentrations of sodium nitrite when compared with the redox methods.

According to the present invention there is provided an automatically controlled continuous process for the diazotisation or tetrazotisation of aromatic amines in which the rate of addition of the inorganic nitrite is controlled by a polarovoltric method.

An example of a polarovoltric detection system which controls the rate of addition of inorganic nitrite consists of a pair of platinum electrodes which are polarised by connecting a suitable constant current across them, for example by means of a 6-volt battery in combination with a series of resistors. The polarisation voltage is indicated by a millivolt meter. The presence of excess nitrite depolarises the electrodes and the voltage drops very sharply. This voltage variation can be used to control the valve used for adding nitrite solution to the reaction vessel either by a simple on/off switch or by continuously regulating the degree of opening of the valve. The millivolt meter/controller can be set at any point along the sharp variation in voltage so that the nitrite supply is decreased or switched off when the voltage falls below the set-point and increased or switched on when the voltage rises above the set-point.

In order to obtain greater sensitivity at the end-point of the reaction it is desirable to use at least two reaction vessels in series with the contents of one overflowing to the next in the series. Each vessel is fitted with a polarovoltric control mechanism. In the case of fast-reacting amines like 3.3'-dichlorbenzidine two vessels are sufficient since the main part of the reaction occurs in the first vessel and the second vessel can be used for fine adjustment of the reaction end-point by selecting a suitable setting on the controller. With weakly-basic amines like 3-nitro-4-aminotoluene which react fairly slowly it is best to use a series of three or perhaps even four vessels again with the fine adjustment taking place in the last vessel. An alternative to the series of separate reactors described above is the multi-stage reactor. This is in effect a series of vessels in which a vertical tube is divided into a number of compartments by a series of horizontal plates. Mixing is carried out by means of a single stirrer, the shaft of which extends vertically down the full length of the mixer through holes in the plates and carries a propellor or other agitator in each compartment. There is sufficient clearance between the stirrer shaft and the plates to allow the reactant mixture to flow down through the full length of the mixer at the rate required by the reaction and at the same time to avoid back-mixing as far as possible. A reactor of this type is made and sold under the Trade Mark "Lightnin Reactor" by Lightnin Mixers Limited. The range of sensitivity of the polarovoltric system enables it to be employed to monitor and control the varying sodium nitrite end point concentrations required in successive vessels. If desired an automatic cooling system may be used to control the temperature of the reaction mixture. For example, the reaction mixture may be circulated through an external heat exchanger using brine supplied from a refrigeration system as a coolant. If two or more reaction vessels are used the amount of heat generated in the second and subsequent reaction vessels is small and sufficient cooling can be obtained either by inserting a cooling coil in the reaction vessels and passing brine through or by using jacketed reaction vessels and passing brine through the jacket.

The process of the present invention may be used for all amines which are diazotisable under aqueous acid conditions. Such diazotisable amines are, for example, primary aromatic amines or polyamines derived from benzene, or from biphenyl, or from condensed benzenoid structures such as naphthalene or anthracene, or from structures in which benzene is condensed with a heterocyclic ring, in which the carbocyclic or heterocyclic aromatic nucleus can be unsubstituted or substituted with one or more of the following groups: alkyl, alkoxy, halogeno, nitro, cyano, acylamino, sulphonamido, carboxylic acid, and sulphonic acid. Examples of diazotisable amines are 2:5 dichloraniline, 3.3'-dichlorbenzidine, 5-nitro-2-aminoanisole, 3-nitro-4-aminotoluene, 4-chloro-2-nitroaniline, 4-amino-toluene-3-sulphonic acid,
4-chloraniline
2:4-dichloraniline
4-nitroaniline
3-nitro-4-aminoanisole
2-chloro-4-nitroaniline
2-amino-anisole-4-sulphodiethylamide
5-chloro-2-amino-toluene
4-chloro-2-amino-toluene
4-nitro-2-amino-toluene
5-nitro-2-amino-toluene
4-nitro-2-amino-anisole
3,3'-dimethoxybenzidine
3,3'-dimethoxy-6,6'-dichlorbenzidine
anthranilic acid methyl ester
2-chloro-4-aminotoluene-5-sulphonic acid
2-chloro-5-aminotoluene-4-sulphonic acid
4-chloroaniline-3-sulphonic acid
aniline-2:5-disulphonic acid
2-chloro-5-aminoethylbenzene-4-sulphonic acid
5-amino-6-methyl-benzimidazolone
4-methyl-6-chloro-7-amino-quinolone
4(-2'-methoxy-4'-amino-5'-chlorophenylamino)-quinazoline
3-amino-dibenzfuran
6-methyl-7-amino-phenomorpholone(3)

The diazotising agent is usually an inorganic nitrite such as sodium nitrite in combination with a mineral acid such as hydrochloric acid.

The diazotised amine solution may be passed to a storage vessel or it may be continuously analysed and afterwards be reacted with a suitable coupling component to form an azo pigment without intermediate storage. This coupling process may also be automatically controlled in the manner described in U.S. Pat. No. 4,159,264.

Figure 2:
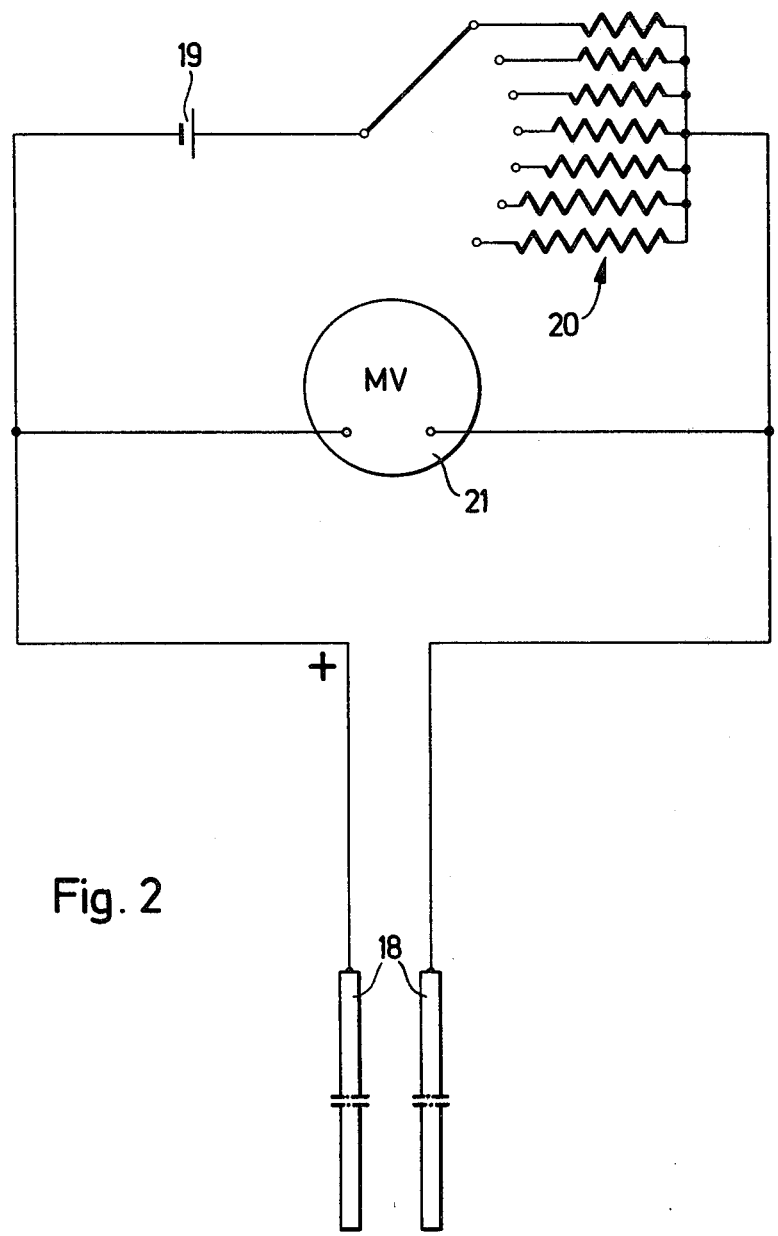

The invention will be further described by way of example with reference to the accompanying drawings in which FIG. 1 represents a diagrammatic view of the plant for a continuous process, FIG. 2 represents a diagrammatic view of the polarovoltric control system.

The system contains three storage vessels 10, 11 and 12. Storage vessel 10 contains diazotisable amine mixed with water and sufficient hydrochloric acid for the reaction, storage vessel 11 contains water, and storage vessel 12 contains sodium nitrite solution. The reaction is carried out in two reactors 13 and 14 in series. The slurry of the diazotisable amine from storage vessel 10 and the water from storage vessel 11 are metered into reactor 13 using metering pumps 15 and 16 respectively at a rate normally set so that the average residence time in the reactor is 30 minutes but this can be varied as required. Sodium nitrite solution from storage vessel 12 is added simultaneously to reactor 13 by means of a valve 17 at such a rate that a slight excess of nitrite is present in the reaction. This is controlled by a potentiometric system in which the detector head is a platinum electrode pair 18 polarised by connecting a suitable constant current across them by means of a 6-volt battery 19 in combination with a series of resistors 20. The polarisation voltage is indicated by a millivolt meter 21.

The temperature in reactor 13 is controlled by circulating the contents by a pump 22 through an external heat exchanger 23 using brine from a refrigeration system as the cooling medium. The flow of brine is controlled by the temperature indicator/controller 33 which operates the valve 24. The reaction medium from reactor 13 overflows to reactor 14 through a coarse strainer 25 which holds back any large unreacted particles. The diazotisation reaction is completed in the jacketed reactor 14 where sodium nitrite solution from storage vessel 12 is added by means of a valve 26 at such a rate that a slight excess of nitrite is present in the reaction. This is controlled in the same manner as described for the process in reactor 13 by a potentiometric system in which the detector head is a platinum electrode pair 18 polarised by connecting a suitable constant current across them. The polarisation voltage is indicated by a millivoltmeter 21. Cooling of reactor 14 is obtained by passing brine, supplied from a refrigeration system through a valve 28 and controlled by a temperature indicator/controller 34, through the jacket.

The diazotised amine solution passes from reactor 14 by pump 29 through clarification filters 30 and 31 arranged in parallel (this allows one to be cleaned while the other is operating) and then to a storage vessel 32. The level of the solution in vessel 14 is controlled by the level indicator/controller 35. When the level is too low, the valve 36 is opened to allow the solution to recirculate to the vessel.

When the level rises above the set point, the controller closes valve 36 and the solution passes through the filter to the storage vessel.

The following Examples further illustrates the present invention.

EXAMPLE 1

In the plant described above one storage vessel contains 3,3'-dichlorobenzidine mixed with water and sufficient hydrochloric acid for the reaction. This is a smooth pumpable slurry containing approximately 20% 3,3'-dichlorobenzidine by weight. One storage vessel contains water and the other contains 40% by weight aqueous solution of sodium nitrite.

The slurry of 3,3'-dichlorobenzidine and water are metered into a first reactor using metering pumps at a rate so that the average residence time in the reactor is 30 minutes. Sodium nitrite solution is added simultaneously at such a rate that a slight excess is present in the reaction this being controlled by the potentiometric system described above and illustrated in FIG. 2. The platinum electrode pair is polarised with a current of 1.0 microamperes. When no unreacted nitrite is present the voltage stays constant at between 600 and 700 millivolts but the presence of excess nitrite depolarises the electrodes and the voltage drops sharply to around 100 millivolts. A millivolt meter/controller is set at a point on the steep part of the curve i.e. between 700 and 300 millivolts to switch off the nitrite supply when the voltage falls below the set-point and switch it on when the voltage rises above the set-point. The temperature in the first reactor is controlled by circulating the contents through an external heat exchanger using brine supplied from a refrigeration system. The reaction medium overflows into a second reactor through a coarse strainer which holds back any large unreacted particles and the diazotisation reaction is completed using exactly the same control mechanism as described for the first reactor except that the platinum electrode pair was polarised with a current of 0.05 microamperes. Cooling is carried out by using a jacketed reactor and passing brine through this jacket. The diazotised amine solution then passes through a clarification filter to a storage vessel.

EXAMPLE 2

Referring to FIG. 1 the storage vessel 10 contains a smooth slurry of 100.0 parts 5-nitro-2-aminoanisole, 181.0 parts hydrochloric acid S.G. 1.18, and 3.0 parts ETHOMEEN C25 made to 1,100 parts with water.

Storage vessel 12 contains a solution of 41.1 parts sodium nitrite made to 100 parts with water.

The slurry is metered to the reactor 13 at such a rate that the average residence time in this reactor is 100 minutes. The addition of sodium nitrite solution from storage vessel 12 to reactor 13 is automatically controlled by the polarovoltric system as in Example 1 so that a slight excess is maintained throughout the reaction. The temperature in reactor 13 is automatically controlled at 0°–2° by the cooling system. The reaction medium passes from reactor 13 to reactor 14 through the coarse strainer 25 and the reaction is completed during an average residence time of 15 minutes in reactor 14 again under the automatic control of the polarovoltric system after which the diazo solution is filtered and passes to storage or further reaction.

EXAMPLE 3

A slurry consisting of 210 parts 2:5-dichloraniline and 460 parts hydrochloric acid made to 4,000 parts with water is metered from storage vessel 10 to reactor 13 at such a rate that the average residence time in reactor 13 is 1 hour. Sodium nitrite solution is added to reactor 13 simultaneously under the control of the polarovoltric system which automatically maintains a slight excess of nitrite in the reaction. The reaction medium then passes to reactor 14 via an overflow and coarse screen and the reaction goes to completion during a further 1 hour residence in this reactor again under the automatic control of the polarovoltric system. The temperature is automatically controlled between 0° C. and 2° C. The diazo solution is filtered and then passed to storage or directly to further reaction e.g. an azo coupling reaction.

What we claim is:

1. In a process for the diazotization of aromatic primary monoamines or diamines which comprises adding regularly and continuously to a reactor (1) an aqueous slurry or solution of the amine containing sufficient acid for the diazotization process and (2) a solution of an inorganic nitrite at a rate which is automatically regulated to ensure that a preselected concentration of unreacted nitrous acid is maintained in the reactor throughout the whole period of the reaction wherein the improvement comprises employing a polarovoltric controller to regulate the rate of addition of the inorganic nitrite so that the concentration of nitrous acid present in the reaction mixture can be controlled to any desired value within certain limits by variation of the polarizing current during the whole period of the reaction.

2. A process as claimed in claim 1 in which the rate of addition of inorganic nitrite is controlled by a pair of platinium electrodes which are polarized by connecting a suitable constant current across them, such that the presence of excess nitrite depolarises the electrodes and causes the voltage to drop sharply, the voltage variation being used to control the valve used for adding the nitrite solution to the reaction vessel.

3. A process as claimed in claim 2 in which the valve is controlled by an on/off switch.

4. A process as claimed in claim 2 in which the valve is controlled by continuously regulating the degree of opening.

5. A process as claimed in claim 1 in which there are used two or more reaction vessels in series with contents of one overflowing to the next in the series, each vessel being fitted with a polarovoltric control mechanism.

6. A process as claimed in claim 5 in which the last reaction vessel is used for fine adjustment of the reaction end-point by selecting a suitable setting on the controller.

7. A process as claimed in claim 1 in which there is used a multi-stage reactor which is a series of vessels in which a vertical tube is divided into a number of compartments by a series of horizontal plates.

8. A process as claimed in claim 1 in which the amine used is one which is diazotizable under aqueous acid conditions.

9. A process as claimed in claim 8 in which the amine used is 2:5-dichloraniline, 3,3'-dichlorbenzidine, 5-nitro-2-aminoanizole, 3-nitro-2-aminotoluene, 4-chloro-2-nitro-aniline or 4-amino-toluene-3-sulphonic acid.

10. A process as claimed in claim 1 in which the diazotising agent is sodium nitrite in combination with hydrochloric acid.

* * * * *